(12) United States Patent
Hutchenson et al.

(10) Patent No.: US 9,181,210 B2
(45) Date of Patent: *Nov. 10, 2015

(54) PROCESSES FOR MAKING FURFURALS

(71) Applicant: E I DU PONT DE NEMOURS AND COMPANY, Wilmington, DE (US)

(72) Inventors: Keith W Hutchenson, Lincoln University, PA (US); Michael Stephen McKinnon, Kingston (CA); Bhuma Rajagopalan, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,436

(22) Filed: Dec. 28, 2012

(65) Prior Publication Data

US 2013/0172582 A1  Jul. 4, 2013

Related U.S. Application Data

(60) Provisional application No. 61/580,740, filed on Dec. 28, 2011.

(51) Int. Cl.
C07D 311/92 (2006.01)
C07D 307/50 (2006.01)

(52) U.S. Cl.
CPC .................... C07D 307/50 (2013.01)

(58) Field of Classification Search
CPC ...................................... C07D 307/50
USPC ......................................... 549/489
See application file for complete search history.

(56) References Cited

U.S. PATENT DOCUMENTS

| | | | |
|---|---|---|---|
| 2,536,732 A | 1/1951 | Dunlop |
| 2,559,607 A | 7/1951 | Dunning |
| 2,750,394 A | 6/1956 | Peniston |
| 4,088,660 A | 5/1978 | Puurunen |
| 4,154,744 A | 5/1979 | Hamada |
| 4,366,322 A | 12/1982 | Raymond |
| 4,503,023 A | 3/1985 | Breck |
| 4,533,743 A | 8/1985 | Medeiros |

(Continued)

FOREIGN PATENT DOCUMENTS

| CN | 100999677 A | 7/2007 |
|---|---|---|
| CN | 101367782 A | 2/2009 |

(Continued)

OTHER PUBLICATIONS

Karinen et al., Biorefining: Heterogeneously Catalyzed Reactions of Carbohydrates for The Production of Furfural and Hydroxymethylfurfural, Chem Sus Chem, vol. 4 (2011), pp. 1002-1016.

(Continued)

*Primary Examiner* — Andrew D Kosar
*Assistant Examiner* — Raymond Covington

(57) ABSTRACT

Processes for making furfural and 5-hydroxymethylfurfural from sugars are provided. The processes can be carried out using a batch process or a continuous mode of operation. An aqueous sugar solution is pressurized with $CO_2$, thereby producing carbonic acid in situ that catalyzes the dehydration reaction to produce furfural from $C_5$ sugars and 5-methylhydroxyfurfural from $C_6$ sugars.

7 Claims, 1 Drawing Sheet

(56) References Cited

U.S. PATENT DOCUMENTS

| | | | |
|---|---|---|---|
| 4,897,497 | A | 1/1990 | Fitzpatrick |
| 5,608,105 | A | 3/1997 | Fitzpatrick |
| 5,859,263 | A | 1/1999 | Ghorpade |
| 6,441,202 | B1 | 8/2002 | Lightner |
| 6,518,440 | B2 | 2/2003 | Lightner |
| 6,743,928 | B1 | 6/2004 | Zeitsch |
| 7,572,925 | B2 | 8/2009 | Dumesic |
| 8,277,521 | B2 | 10/2012 | Gruter |
| 8,314,260 | B2 | 11/2012 | Gruter |
| 8,389,749 | B2 | 3/2013 | Dumesic |
| 8,399,688 | B2 | 3/2013 | Dumesic |
| 2003/0032819 | A1 | 2/2003 | Lightner |
| 2007/0298477 | A1 | 12/2007 | Kratochvil |
| 2008/0033187 | A1 | 2/2008 | Zhao |
| 2008/0033188 | A1 | 2/2008 | Dumesic |
| 2009/0124839 | A1 | 5/2009 | Dumesic |
| 2009/0131690 | A1 | 5/2009 | Gruter et al. |
| 2009/0156841 | A1 | 6/2009 | Sanborn et al. |
| 2009/0194407 | A1 | 8/2009 | Tang |
| 2009/0306415 | A1 | 12/2009 | Gruter |
| 2010/0048924 | A1 | 2/2010 | Kilambi |
| 2010/0058650 | A1 | 3/2010 | Gruter |
| 2010/0212218 | A1 | 8/2010 | Gruter |
| 2010/0218415 | A1 | 9/2010 | Gruter |
| 2010/0218416 | A1 | 9/2010 | Gruter |
| 2010/0299991 | A1 | 12/2010 | Gruter |
| 2010/0317879 | A1 | 12/2010 | Zhao |
| 2011/0065159 | A1 | 3/2011 | Raines |
| 2011/0071306 | A1 | 3/2011 | Robinson |
| 2011/0144359 | A1 | 6/2011 | Van Der Heide |
| 2012/0108829 | A1 | 5/2012 | De Jong |
| 2012/0111714 | A1 | 5/2012 | Court |
| 2012/0157697 | A1 | 6/2012 | Burket |
| 2013/0017579 | A1 | 1/2013 | Luterbacher |

FOREIGN PATENT DOCUMENTS

| | | | |
|---|---|---|---|
| CN | 101486695 | A | 7/2009 |
| CN | 101130530 | A | 11/2010 |
| EP | 1834950 | A1 | 9/2007 |
| EP | 1834951 | A1 | 9/2007 |
| EP | 2033958 | A1 | 3/2009 |
| GB | 799603 | A | 8/1958 |
| GB | 838957 | A | 6/1960 |
| JP | 02-108682 | A | 4/1990 |
| JP | 12065468 | A | 10/1998 |
| JP | 2007196174 | A | 8/2007 |
| WO | 2008151178 | A1 | 12/2008 |
| WO | 2009030504 | A2 | 3/2009 |
| WO | 2009030506 | A2 | 3/2009 |
| WO | 2009030507 | A2 | 3/2009 |
| WO | 2009030508 | A2 | 3/2009 |
| WO | 2009030510 | A2 | 3/2009 |
| WO | 2009030511 | A1 | 3/2009 |
| WO | 2009030512 | A2 | 3/2009 |
| WO | 2010124381 | A1 | 11/2010 |
| WO | 2011063500 | A1 | 6/2011 |
| WO | 2011126654 | A2 | 10/2011 |

OTHER PUBLICATIONS

Gairola et al., Hydrothermal Pentose to Furfural Conversion and Simultaneous Extraction With Sc—Co2, Kinectics and Application to Biomass Hydrolysates, Bioresource Technology, vol. 123 (2012), pp. 592-598.

International Search Report, PCT International Application No. PCT/2012/071940, Mailed Apr. 26, 2013.

E. I. Fulmer et al., The Production of Furfural From Xylose Solutions by Means of Hydrochloric Acid-Sodium Chloride Systems, Department of Chemistry, Iowa, Journal of Physical Chemistry, vol. 40 (1936), pp. 133-41.

C. Liu et al., The Enhancement of Xylose Monomer and Xylotriose Degradation by Inorganic Salts in Aqueous Solutions At 180oC, Carbohydrate Research, vol. 341 (2006), pp. 2550-2556.

G. Marcotullio et al., Chloride Ions Enhance Furfural Formation From D-Xylose in Dilute Aqueous Acidic Solutions, Green Chemistry (2010), The Royal Society of Chemistry, pp. 1-8.

F. Tao et al., Efficient Process for the Conversion of Xylose to Furfural With Acidic Ionic Liquid, Can. J. Chem., vol. 89 (2011), pp. 83-87.

Blatter et al., The Preparation of Pure Zeolite Nay and Its Conversion to High-Silican Faujasite, J. Chem Ed., vol. 67 (1990), pp. 519-521.

Hutchings et al., Developments in the Production of Methyl Tert-Butyl Ether, Catalysis Today, vol. 15 (1992) pp. 23-49.

Baerlocher et al., Atlas of Zeolite Framework Types, $6^{th}$ Revised Edition, Elsevier, Amsterdam, 2007 (Book-Not Included).

Karinen et al., Biorefining: Heterogeneously Catalyzed Reactions of Carbohydrates for the Production of Furfural and Hydroxymethylfurfural, Chem Sus Chem, vol. 4 (2011) pp. 1002-1016.

Chen, Hydrophobic Properties of Zeolites, Journal of Physical Chemistry, vol. 80, No. 1 (1976) pp. 60-64.

Dwyer, Zeolite Structure, Composition and Catalysis, Chemistry and Industry, vol. 2 (1984) pp. 258-269.

Szostak, Molecular Seives Principles of Synthesis and Identification, van Nostr and Reinhold, New York, 1989 (Book-Not Included).

Gairola et al., Hydrothermal Pentose to Furfural Conversion and Simultaneous Extraction With Sc-CO2, Kinetics and Application to Biomass Hydrolysates, Bioresource Technology, vol. 123 (2012), pp. 592-598.

Kawamoto et al., Catalytic Pyrolysis of Cellulose in Sulfolane With Some Acidic Catalysts, J Wood Sci, vol. 53 (2007), pp. 127-133.

Suzuki et al., Dehydration of Xylose Over Sulfated Tin Oxide Catalyst: Influences of the Preparation Conditions on the Structural Properties and Catalytic Performance, Applied Catalysis A: General, vol. 408 (2011), pp. 117-124.

Starr et al., High Sulfidity Pulping in Aqueous Sulfolane, Tappi Alkaline Pulping Conference Preprints (1975), pp. 195-198.

Clermont, Delignification of Aspen Wood With Aqueous Sulfolane Solutions, Tappi, vol. 53, No. 12 (1970), pp. 2243-2245.

Chheda et al., Production of 5-Hydroxymethylfufual and furfural by dehydration of biomass-derived mono- and polysaccharides, Green Chemistry, 2007, 342-350, 9, The Royal Society of Chemistry.

Mamman et al., Furfural: Hemicellulose/xylose-derived biochemical, Biofuels, Bioproducts & Biorefining, 2008, 438-453, Wiley Interscience.

Vazquez et al., Hydrolysis of Sorghum Straw using Phosphoric Acid: Evaluation of Furfural Production, Bioresource Technology, 2007, 3053-3060, 98, Elsevier.

Amiri et al., Production of furans from rice straw by single-phase and biphasic systems, Carbohydrate Research, 2010, 2133-2138, vol. 345.

Weingarten et al., Kinetics of furfural production by dehydration of xylose in a biphasic reactor with microwave heating, Green Chemistry, The Royal Society of Chemistry, 2010, 1423-1429, vol. 12.

Zhao et al., Metal Chlorides in Ionic Liquid Solvents Convert Sugars to 5-Hydroxymethylfurfural, Science, 2007, 1597-1600, vol. 316.

Dias et al., Dehydration of xylose into furfural over micro-mesoporous sulfonic acid catalysts, Journal of Catalysis, 2005, 414-423, vol. 229.

US Non-Final Office Action for U.S. Appl. No. 13/729,526; dated Jun. 19, 2015.

PROCESSES FOR MAKING FURFURALS

FIELD OF THE INVENTION

The present invention is directed to processes for producing furfural and related compounds from sugars.

BACKGROUND

Furfurals are important intermediates for synthesis of value-added chemicals. Furfural and related compounds, such as hydroxy methyl furfural (HMF), are useful precursors and starting materials for industrial chemicals for use as pharmaceuticals, herbicides, stabilizers, and also for making polymers.

While furfural is commercially produced today, HMF is not produced on an industrial scale. One current furfural manufacturing process utilizes biomass such as corn cobs as a raw material feedstock for obtaining xylose or hemicellulose. The hemicellulose is hydrolyzed under acidic conditions to its monomer sugars, such as glucose, fructose, xylose, mannose, galactose, rhamnose, and arabinose. Xylose, which is a pentose (i.e., a "$C_5$ sugar") is the sugar present in the largest amount. In a similar aqueous acidic environment, the $C_5$ sugars are subsequently dehydrated and cyclized to furfural.

A major difficulty with known methods for dehydration of sugars is the formation of undesirable resinous material that not only leads to yield loss but also leads to fouling of exposed reaction vessel surfaces and negatively impacts heat transfer characteristics. A review by R. Karinen et al. (*ChemSusChem* 4 (2011), pp. 1002-1016) includes several commonly used methods of producing furfural generally as described above. All of those methods involve use of a soluble inorganic acid catalyst, such as sulfuric, phosphoric, or hydrochloric acid. These acids are difficult to separate from the final product. Low yields can result from formation of undesirable acid byproducts and resinous material called humins. Mass transfer limitations may also impose restrictions on furfural yield, especially in the use of solid biomass as feedstock. Further, the use of mineral acids requires special materials of construction due to associated corrosion issues, thereby incurring increased capital costs. Environmental emission issues are also of concern. During the commercial production of furfural, yields of only about 50-55% are typically achieved.

WO 2011/126654 discloses a biomass pretreatment method in which the biomass material is subjected to a biphasic mixture of water and supercritical $CO_2$ at a temperature in the range of 150° C. to 250° C. under high pressure (74 to 300 bar, 7.4 to 30 MPa) for a time of from 10 seconds to 100 minutes. In particular embodiments, the process is performed as a two-stage temperature process, wherein an initial, short high-temperature stage is conducted at a temperature of at least 200° C. for up to 20 minutes, and a subsequent, longer low-temperature stage is conducted at a temperature of at least 140° C. and up to 190° C. for 10 to 120 minutes. The process disclosed is designed to maximize sugar yields while minimizing the conversion of these sugars to furfurals. Furfurals are considered to be an unwanted byproduct.

There remains a need for processes for producing furfural and related compounds from sugars at high yield, while minimizing the formation of other byproducts such as acids and undesirable humins.

SUMMARY OF THE INVENTION

One aspect of the present invention is a batch mode process comprising:

a) providing, in a reaction vessel, an aqueous sugar solution comprising at least one $C_5$ sugar, at least one $C_6$ sugar, or a mixture of at least one $C_5$ sugar and at least one $C_6$ sugar, and optionally a water-miscible organic co-solvent; and b) adding the solution to the reaction vessel and pressurizing with $CO_2$ under agitation to form a reaction mixture;

c) maintaining the reaction mixture at a temperature within a range of from about 90° C. to about 220° C., and a pressure within a range of from 0.1 MPa to about 30 MPa, for a time sufficient to effect a reaction to produce a reaction product comprising:
  i) furfural and/or 5-hydroxymethyl furfural,
  ii) water, and
  iii) an aqueous condensate comprising insoluble humins;

d) quenching the reaction mixture to a temperature of about room temperature, e) collecting the aqueous condensate from the reaction mixture upon depressurisation through a single or multistage column; and f) collecting the reaction vessel contents and separating the furfural and/or 5-hydroxymethyl furfural from the reaction vessel contents, and separating the insoluble humins.

Another aspect of the invention is a process comprising contacting an aqueous sugar solution with $CO_2$ in a continuous mode of operation, the process comprising:

a) providing an aqueous sugar solution comprising at least one $C_5$ sugar, at least one $C_6$ sugar, or a mixture of at least one $C_5$ sugar and at least one $C_6$ sugar;

b) providing a reaction vessel;

c) continuously adding the sugar solution to the reaction vessel and pressurizing with $CO_2$ under agitation to form a reaction mixture, wherein the temperature of the reaction mixture is within a range of from about 90° C. to about 220° C., and the operating pressure is between 0.1 MPa and about 30 MPa;

d) maintaining the reaction mixture temperature and pressure for a time sufficient to effect a reaction to produce a reaction product comprising:
  i) furfural and/or 5-hydroxymethyl furfural,
  ii) water, and
  iii) an aqueous condensate comprising insoluble humins;

e) continuously feeding and removing sugar solution, $CO_2$, or both, from the reaction vessel;

f) removing vapors of water and furfural and/or 5-hydroxymethylfurfural from the reaction mixture through a single or multistage column; and g) removing water, furfural and/or HMF from the reaction vessel through a separation device.

In an aspect, there is a process comprising:

a) providing in a reaction vessel, an aqueous sugar solution comprising at least one $C_5$ sugar, at least one $C_6$ sugar, or a mixture of at least one $C_5$ sugar and at least one $C_6$ sugar, and optionally a water-miscible organic co-solvent; and b) adding the solution to the reaction vessel and pressurizing with $CO_2$ under agitation to form a reaction mixture;

c) maintaining the reaction mixture at a temperature in a range of 90-220° C., and a pressure in a range of 0.1-30 MPa, for a time sufficient to produce a mixture comprising one or more of furfural, 5-hydroxymethyl furfural and water;

d) quenching the reaction mixture to room temperature and depressurizing the reaction vessel into a condenser to form a condensate, wherein the condensate comprises one or more of humins, furfural, 5-hydroxymethyl furfural and water, and wherein the reaction vessel contents comprise one or more of furfural, 5-hydroxymethyl furfural, water and unreacted sugar; and e) collecting the reaction vessel contents and separating the furfural and/or 5-hydroxymethyl furfural from the reaction vessel contents, and separating the insoluble humins.

DETAILED DESCRIPTION

Figure 1:
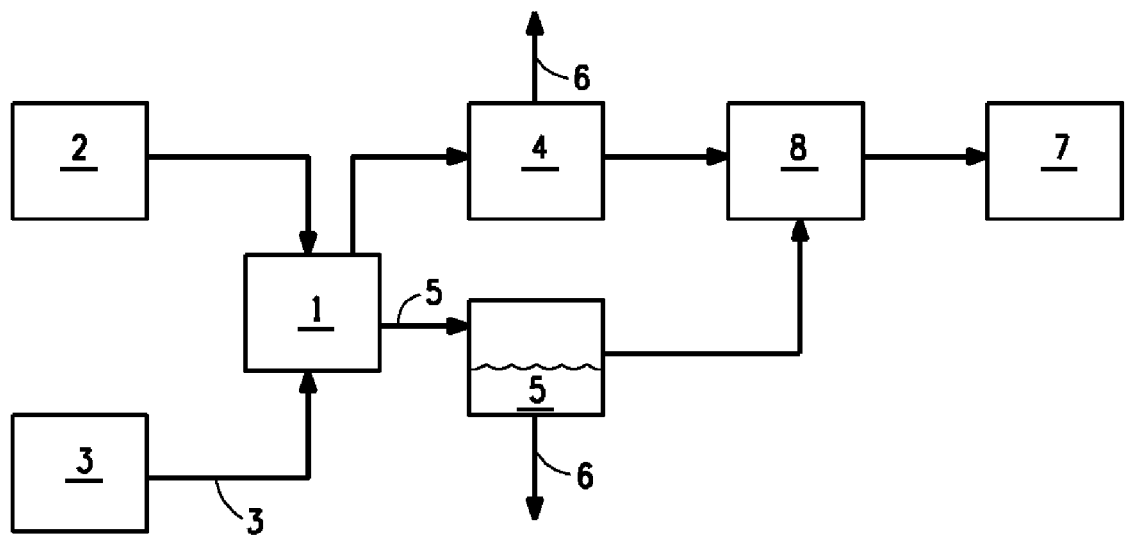
FIG. 1 is a schematic representation of one embodiment of the processes disclosed herein, as operated in a batch mode.

Disclosed herein are methods for making furfurals that utilize $CO_2$ at much lower pressures (tens of bars) than conventional processes and maximize production of furfurals and related compounds such as HMF from both sugar and biomass. The methods disclosed herein are particularly advantageous in biomass conversion or bio-refinery type plants wherein both $CO_2$ and aqueous sugar streams are both readily available. This technology also improves utilization and sequestration of $CO_2$.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the term "sugar" includes monosaccharides, disaccharides, and oligosaccharides. Monosaccharides, or "simple sugars," are aldehyde or ketone derivatives of straight-chain polyhydroxy alcohols containing at least three carbon atoms. A pentose is a monosaccharide having five carbon atoms; some examples are xylose, arabinose, lyxose and ribose. A hexose is a monosaccharide having six carbon atoms; some examples are glucose and fructose. Disaccharide molecules (e.g., sucrose, lactose, and maltose) consist of two covalently linked monosaccharide units. As used herein, "oligosaccharide" molecules consist of about 3 to about 20 covalently linked monosaccharide units.

As used herein, the term "$C_n$ sugar" includes: monosaccharides having n carbon atoms; disaccharides comprising monosaccharide units having n carbon atoms; and oligosaccharides comprising monosaccharide units having n carbon atoms. Thus, "$C_5$ sugar" includes pentoses, disaccharides comprising pentose units, and oligosaccharides comprising pentose units.

As used herein, the term "hemicellulose" refers to a polymer comprising $C_5$ and $C_6$ monosaccharide units. Hemicellulose consists of short, highly branched chains of sugars. In contrast to cellulose, which is a polymer of only glucose, a hemicellulose is a heterogeneous polymer comprising several different sugars, and its specific composition can vary with its source. It contains five-carbon sugars (usually D-xylose and L-arabinose) and six-carbon sugars (D-galactose, D-glucose, D-fructose, L-rhamnose, and D-mannose). Hemicellulose can also contain uronic acid, sugars in which the terminal carbon's hydroxyl group has been oxidized to a carboxylic acid, such as, D-glucuronic acid, 4-O-methyl-D-glucuronic acid, and D-galacturonic acid. The sugars are partially acetylated. Typically the acetyl content is 2 to 3% by weight of the total weight of the hemicellulose. Xylose is typically the sugar monomer present in hemicellulose in the largest amount.

As used herein, the term "organic" denotes carbon-containing compounds with the following exceptions: binary compounds as the carbon oxides, carbides, and carbon disulfide; ternary compounds such as metallic cyanides, metallic carbonyls, phosgene, and carbonyl sulfide; and metallic carbonates such as calcium carbonate and sodium carbonate.

As used herein, the term "catalytic amount" means a sub-stoichiometric amount of catalyst relative to a reactant.

As used herein, the term "organic acid" means an organic compound having acidic properties. Some examples are acetic acid, formic acid, and methane sulfonic acid.

As used herein, the term "high boiling" denotes a solvent having a boiling point above about 100° C. at a pressure of one atmosphere.

As used herein the term "water-miscible organic solvent" refers to an organic solvent that can form a monophasic solution with water at the temperature at which the reaction is carried out.

As used herein the term "humin(s)" refers to dark, amorphous byproduct(s) resulting from acid-induced sugar and furfural degradation.

As used herein, the term "selectivity" refers to the moles of furfural produced, divided by the moles of xylose transformed to products over a particular time period.

The acid catalyst is water-soluble and comprises a mineral acid, a heteropolyacid, an organic acid, or a combination thereof. In one embodiment, the acid catalyst is a mineral acid comprising sulfuric acid, phosphoric acid, hydrochloric acid, or a combination of these. In one embodiment, the acid catalyst is a heteropolyacid comprising phosphotungstic acid, molybdophosphoric acid, or a combination of these. In one embodiment, the acid catalyst is an organic acid comprising oxalic acid, formic acid, acetic acid, an alkyl sulfonic acid, an aryl sulfonic acid, a halogenated acetic acid, a halogenated alkylsulfonic acid, a halogenated aryl sulfonic acid, or a combination of these. An example of a suitable alkyl sulfonic acid is methane sulfonic acid. An example of a suitable aryl sulfonic acid is toluenesulfonic acid. An example of a suitable halogenated acetic acid is trichloroacetic acid. An example of a suitable halogenated alkylsulfonic acid is 1,1,2,2-tetrafluoroethanesulfonic acid. An example of a suitable halogenated aryl sulfonic acid is fluorobenzenesulfonic acid. As used herein, the term "super acid" refers to acids such triflic acid and trifluoromethane sulfonic acid. Use of the term "heterogeneous catalyst" refers to any solid material containing Brönsted and/or Lewis acid sites, and which is substantially insoluble in the reaction medium under ambient and/or operating reaction conditions. These include zeolites, sulfated zirconia, and supported Nafion® perfluorinated sulfonic acid resin catalysts. As used herein, the term "heteropolyacid" denotes an oxygen-containing acid with P, As, Si, or B as a central atom which is connected via oxygen bridges to W, Mo or V. Some examples are phosphotungstic acid and molybdophosphoric acid.

The processes disclosed herein can be used to synthesize furfural and 5-hydroxymethyl furfural (HMF) from sugar streams. The processes can be used when aqueous streams with sugars (pentoses and/or hexoses) are readily available.

The processes disclosed herein involve the use of carbonic acid as a catalyst. The sugar is dissolved in water and is pressurized with $CO_2$ at a fixed temperature. In an embodiment, the pressure is between about 1 bar (0.1 MPa) and about 100 bars (10 MPa). In some embodiments, the pressure is between and optionally including any two of the following values: 1, 5, 10, 20, 30, 40, 50, 60, 70, 80, 90, and 100 bars. The reaction between $CO_2$ and water forms carbonic acid in situ that catalyses the dehydration reactions producing furfural from $C_5$ sugars and 5-hydroxymethylfurfural from $C_6$ sugars.

Acid strength plays a key role in maximising selectivity to furfural and related compounds. Too low an acid strength leads to low conversion, while too high an acid strength increases humins formation. Carbonic acid is an acid with moderate acidity, and the acidity of the medium can be controlled by tuning the $CO_2$ pressure. Advantages of this system are:
1. No external catalyst is required; the catalyst (carbonic acid) is generated in situ.
2. By tuning the $CO_2$ pressure, it is possible to adjust the pH of the aqueous medium to 2-4, thereby optimizing the yield to furfurals (furfural and 5-hydroxymethylfurfural).
3. Optionally, organic solvents and other homogeneous and/ or heterogeneous acid catalysts can also be used.
4. Higher furfural yield and lower humin formation is observed in the batch mode.
5. The reaction is performed at moderate pressures i.e., less than 100 bars (10 MPa).
6. There is a preferential separation of humins during reaction and post-processing. This allows for easy reaction vessel clean-up.

When the reaction is carried out using a 2 wt % xylose solution as feedstock with sulfuric acid as the catalyst, instead of carbonic acid, at comparable pH, the yield of furfural is only 15%, while it is about 35% with the $CO_2$-water system. With inorganic acids such as sulfuric acid, at the end of the reaction, typically a layer of resin is formed on the surface of the reaction vessel that is hard to clean. However, with $CO_2$-water, the reaction vessel surface is relatively cleaner post-reaction.

When reactions are performed in the batch mode, on quenching the reaction mixture to room temperature post-reaction (within 10-15 min), preferential separation of humins is evident. It is important to remove the furfural as it formed thereby preventing degradation of furfural to, e.g., formic acid. In addition, the use of $CO_2$ helps in maintaining acidity as the $CO_2$ continuously dissolves in water. The $CO_2$-water system can also be used to directly convert solid biomass such as corn cob to furfurals, including 5-hydroxymethylfurfural (HMF) and furfural.

In one embodiment, a batch mode of operation, with reference to FIG. 1, the reaction vessel 1 is charged initially with an aqueous feedstock solution 2 containing $C_5$ and/or $C_6$ sugar(s), which is added over time. The feedstock can be charged to a preheated reaction vessel, or the reaction vessel can be heated after the feedstock has been added. The reaction vessel is then pressurised with a $CO_2$ gas stream 3 to the desired pressure. The reaction vessel 1 is then isolated from both the input and output streams and maintained at the desired temperature and pressure for the desired time period, during which the sugar undergoes chemical transformation to furfural. At the end of the desired reaction time, the reaction vessel 1 is quenched to room temperature using ice-water for 10-15 minutes and depressurized into a condenser unit 4. Post-reaction contents of the reaction vessel include furfural, unreacted sugar and unwanted byproducts that constitute stream 5. The condensate from the condenser unit 4 and stream 5 can be filtered to remove the humins 6, and the furfural 8 can be separated from the water 7 and purified by any convenient methods known in the art. The unreacted sugars can be separated and recycled back to the reaction vessel 1.

Figure 2:
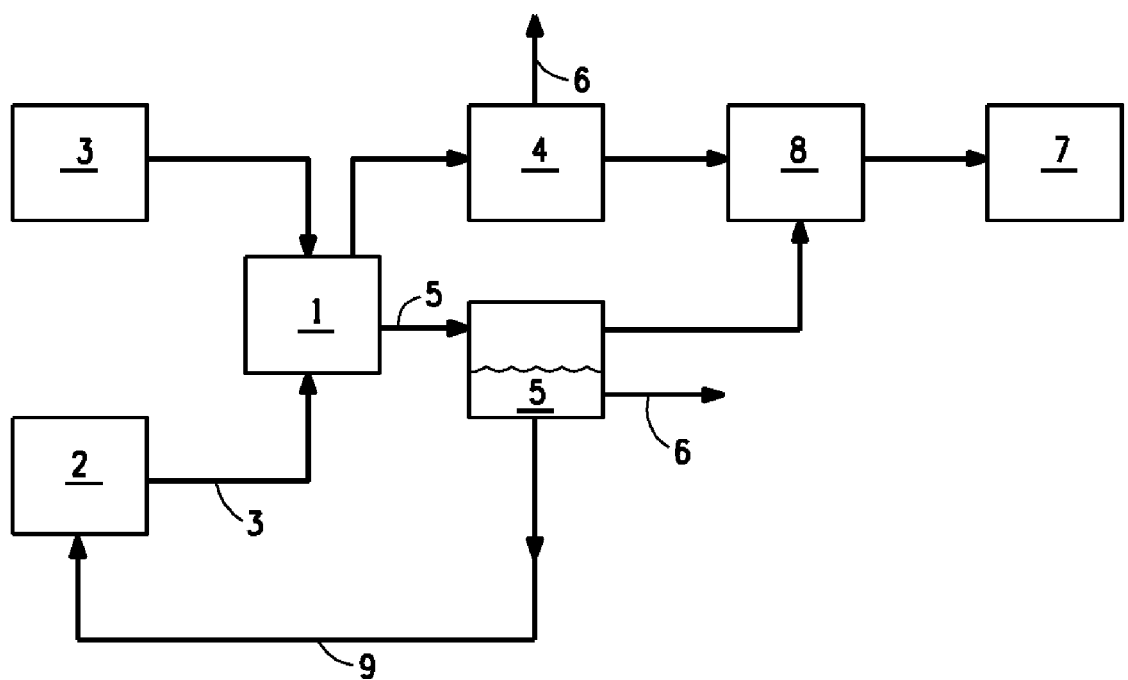
FIG. 2 is a schematic representation of one embodiment of the processes disclosed herein, as operated in a continuous/semi-continuous mode.

In another embodiment, a continuous mode, with reference to FIG. 2, the preheated reaction vessel 1 is charged continuously with an aqueous feedstock solution 2 containing $C_5$ sugar and/or $C_6$ sugar and pressurised with $CO_2$ gas stream (3) to the desired pressure. The reaction vessel 1 is maintained at the desired temperature and pressure so that the sugar undergoes chemical transformation to furfural and the product is continuously removed from the vapor phase using a condenser 4 or a multistage distillation unit. The condenser can be used as an online or offline unit. The condensate from the condenser unit 4 can also be subject to a filtration 6 and then the furfural can be purified by distillation to provide the final product furfural 8. The liquid phase 5 is also continuously removed and is filtered to remove the humins 6. The furfural 8 can be separated from the water 7 and purified by any convenient methods known in the art. The unreacted sugar solution 9 is then recycled back to the reaction vessel 1.

In some embodiments, solid biomass can also be used. In some embodiments the $CO_2$ can be added and removed continuously so as to facilitate continuous stripping of furfural. Any $CO_2$ that remains in the liquid phase can also be recovered (e.g., by depressurization followed by conventional separation techniques) and recovered. In some embodiments, a liquid or vapor stream can be continuously removed to effect a semi-continuous operation. In some embodiments, both liquid and vapor streams can be continuously fed and continuously removed from the reaction vessel. In some embodiments, both liquid and vapor streams are continuously fed and continuously removed using a column or tubular reaction vessel configuration. In some embodiments, both liquid and vapor streams are continuously fed and continuously removed using a fluidised bed configuration. In some embodiments, both liquid and vapor streams are continuously fed and continuously removed in a stirred vessel. In some embodiments, both liquid and vapor streams are continuously fed and continuously removed in a reactive distillation setup.

In preferred embodiments, the process is carried out without added catalyst, i.e., using in situ generated carbonic acid as catalyst. In some embodiments, the process is carried out with added catalyst, i.e., mineral acid and/or super acid and/or solid acid catalyst in addition to in situ generated carbonic acid as catalyst.

The process disclosed herein facilitates preferential separation of humins. Undesirable humins that are formed as products during these dehydration reactions form a separate phase, thereby making it easy to separate them from the reaction system. Removal of humins into a separate phase also mitigates yield losses to furfural by preventing reaction of humins with the desired furfural product in the reaction phase.

In some embodiments, the process utilizes $CO_2$ as a stripping agent to remove furfural from the reaction phase. In some embodiments, the process utilises $CO_2$ as an extracting agent when solids, i.e., biomass and/or heterogeneous catalysts, are used in the process.

In an embodiment, the conversion of sugar to furfural is in the range of 10-100% or 25-100% or 50-100%. In another embodiment, the furfural selectivity is in the range of 10-95% or 10-85% or 12-65%.

Various features and/or embodiments of this invention are illustrated in drawings as described herein. These features and/or embodiments are representative only, and the selection of these features and/or embodiments for inclusion in the drawings should not be interpreted as an indication that subject matter not included in the drawings is not suitable for practicing the invention, or that subject matter not included in the drawings is excluded from the scope of the appended claims and equivalents thereof.

EXAMPLES

The methods described herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

Abbreviations

The meaning of abbreviations is as follows: "DMSO" means dimethylsulfoxide, "g" means gram(s), "LC" means liquid chromatography, "mg" means milligram(s), "mL" means milliliter(s), "MPa" means megapascal(s), "psi" means pounds per square inch, "RID" means refraction index detector, "Conv." means conversion, and "wt %" means weight percent(age).

Materials

Xylose (99% purity, catalog number X1500) was obtained from Sigma-Aldrich Corporation (St. Louis, Mo.), D-(–)Fructose was also obtained from Sigma-Aldrich Corporation (99% purity, catalog number F0127, batch: 128K1163).

Deionized water was used.

Ultra high purity grade nitrogen and $CO_2$ from Airgas®

Sulfuric acid was obtained from EMD Chemicals, Inc. (catalog number SX1244-6).

General Procedure for Examples 1-5 and Comparative Examples A-C

For each run, 50 g of sugar solution (xylose or fructose, as indicated, typically 2-10 wt %) was charged into a 100 mL Hastelloy Parr reaction vessel. Where sulfuric acid was used, 0.01 g was added along with the sugar solution. The reaction vessel was sealed and pressurized to 200 psi (1.38 MPa, $CO_2$ or nitrogen). The reaction vessel was heated to the indicated reaction temperature. Once the reaction temperature was attained, the reaction vessel pressure was also increased to the desired levels. This was considered the start of the reaction. The reactions were typically performed for an hour. At the end of the run, the reaction was quenched to 40° C. by putting the reactor vessel in an ice-water bath. The reaction vessel was depressurized through the vapor port into a cold finger placed in an ice-water bath. The reaction vessel was disassembled and the liquid was collected. The condensate on the cold finger and the post-reaction liquid from the reaction vessel were weighed. The samples were analyzed using an Agilent Technologies (Santa Clara, Calif.) LC-RID system, with DMSO as an internal standard added at 5 mg DMSO per gram of reaction mixture. The experimental conditions and results for each run are given in Table 1.

TABLE 1

Summary of data for sugar dehydration to furfurals*

| Run | Starting feed sugar Xylose(X) Fructose(F) | Temp (° C.) | Catalyst added | Gas added | Conv. (%) | Selectivity to furfural (%) | Selectivity to formic acid** (%) |
|---|---|---|---|---|---|---|---|
| Comp. Ex. A | X | 160 | $H_2SO_4$ | $N_2$ | 60 | 10 | 2 |
| Comp. Ex. B | X | 170 | $H_2SO_4$ | $N_2$ | 75 | 33 | 6 |
| Comp. Ex. C | X | 180 | $H_2SO_4$ | $N_2$ | 92 | 26 | 5 |
| Ex. 1 | X | 180 | $H_2SO_4$ | $CO_2$ | 89 | 35 | 35 |
| Ex. 2 | X | 160 | none | $CO_2$ | 71 | 16 | 35 |
| Ex. 3 | X | 170 | none | $CO_2$ | 89 | 15 | 20 |
| Ex. 4 | X | 180 | none | $CO_2$ | 97 | 19 | 18 |
| Ex. 5 | F | 180 | none | $CO_2$ | 70 | 25 | |

*Initial concentration of sugar: 2 wt %
**Formic acid is a degradation product of furfural.

Examples 2, 3 and 4 demonstrate that the use of $CO_2$-water system is effective in producing furfural. For reactions with nitrogen and sulfuric acid (Comparative Examples A, B and C) the initial pH was targeted at 2.2-2.4 to be in comparable to the pH of carbonic acid formed in the $CO_2$-water system in the Examples 2, 3 and 4. With the use of $CO_2$ in place of nitrogen, as shown in Example 1, the sugar conversions increase and the sum of furfural and formic acid produced is also elevated. As a consequence, the amount of humins formed is lowered when one utilizes carbonic acid, i.e., a $CO_2$-water system, compared to using sulfuric acid with nitrogen. One also observes higher amounts of formic acid with the $CO_2$-water system, possibly likely due to degradation of furfural in the reaction phase. Example 5 shows feasibility of HMF production in this reaction system.

Similar observation of higher sugar conversion and higher furfural and formic acid is also seen in Example 1 with the use of sulfuric acid in addition to the carbonic acid catalyst. Relatively high furfural selectivity of ~35% is obtained in this example, with nearly equal selectivity to formic acid. Lower dark material, i.e., humins, are observed in Example 1. The formic acid is likely formed due to degradation of furfural in the reaction phase, and one may reduce this degradation by continuous removal of furfural from the reaction phase as soon as it forms, as discussed above. When sulfuric acid is used as a catalyst with nitrogen as the inert gas, lower conversion and furfural selectivity are obtained (Comparative Example A). It is to be noted that the reaction with $CO_2$ is catalyzed by carbonic acid in addition to the added sulfuric acid.

The invention claimed is:
1. A process comprising:
a) providing, in a reaction vessel, an aqueous sugar solution comprising at least one $C_5$ sugar, at least one $C_6$ sugar, or a mixture of at least one $C_5$ sugar and at least one $C_6$ sugar, and optionally a water-miscible organic co-solvent; and b) adding the solution to the reaction vessel and pressurizing with $CO_2$ under agitation to form a reaction mixture;

c) maintaining the reaction mixture at a temperature within a range of from about 90° C. to about 220° C., and a pressure within a range of from 0.1 MPa to about 30 MPa, for a time sufficient to effect a reaction to produce a reaction product comprising:
 i) furfural and/or 5-hydroxymethyl furfural,
 ii) water, and
 iii) an aqueous condensate comprising insoluble humins;

d) quenching the reaction mixture to a temperature of about room temperature;

e) collecting the aqueous condensate from the reaction mixture upon depressurisation through a single or multistage column; and f) collecting the reaction vessel contents and separating the furfural and/or 5-hydroxymethyl furfural from the reaction vessel contents, and separating the insoluble humins, wherein said process is conducted in a Batch mode.

2. A process comprising contacting an aqueous sugar solution with $CO_2$ in a continuous mode of operation, the process comprising:
 a) providing an aqueous sugar solution comprising at least one $C_5$ sugar, at least one $C_6$ sugar, or a mixture of at least one $C_5$ sugar and at least one $C_6$ sugar;
 b) providing a reaction vessel;
 c) continuously adding the sugar solution to the reaction vessel and $CO_2$ under agitation to form a reaction mixture, wherein the temperature of the reaction mixture is within a range of from about 90° C. to about 220° C., and the operating pressure is between 0.1 MPa and about 30 MPa;
 d) maintaining the reaction mixture temperature and pressure for a time sufficient to effect a reaction to produce a reaction product comprising:
  i) furfural and/or 5-hydroxymethyl furfural,
  ii) water, and
  iii) an aqueous condensate comprising insoluble humins;
 e) continuously feeding and removing sugar solution, $CO_2$, or both from the reaction vessel;
 f) removing vapors of water and furfural and/or 5-hydroxymethylfurfural from the reaction mixture through a single or multistage column; and
 g) removing liquid from the reaction vessel through a separation device.

3. The process of claim 1, wherein the aqueous sugar solution comprises a water-miscible organic co-solvent selected from the group consisting of sulfolane, acetonitrile, and THF.

4. The process of claim 3 wherein the aqueous sugar solution further comprises an acid catalyst selected from the group consisting of a mineral acid, a superacid, a heteropolyacid, an organic acid, a solid acid catalyst and combinations thereof, and the acid catalyst is present at about 0.01 weight percent to about 10 weight percent as a percentage of the weight of the solvent.

5. The process according to claim 1 or 2, wherein the combined concentration of $C_5$ sugar and/or $C_6$ sugar in the aqueous sugar solution is in the range of 0.5-90 weight percent based on the total weight of the aqueous sugar solution.

6. The process according to claim 1 or 2, wherein the combined concentration of $C_5$ sugar and/or $C_6$ sugar in the aqueous sugar solution is in the range of 0.5-50 weight percent based on the total weight of the aqueous sugar solution.

7. A process comprising:
 a) providing in a reaction vessel, an aqueous sugar solution comprising at least one $C_5$ sugar, at least one $C_6$ sugar, or a mixture of at least one $C_5$ sugar and at least one $C_6$ sugar, and optionally a water-miscible organic co-solvent; and
 b) adding the solution to the reaction vessel and pressurizing with $CO_2$ under agitation to form a reaction mixture;
 c) maintaining the reaction mixture at a temperature in a range of 90-220° C., and a pressure in a range of 0.1-30 MPa, for a time sufficient to produce a mixture comprising one or more of furfural, 5-hydroxymethyl furfural and water;
 d) quenching the reaction mixture to room temperature and depressurizing the reaction vessel into a condenser to form a condensate, wherein the condensate comprises one or more of humins, furfural, 5-hydroxymethyl furfural and water, and wherein the reaction vessel contents comprise one or more of furfural, 5-hydroxymethyl furfural, water and unreacted sugar; and
 e) collecting the reaction vessel contents and separating the furfural and/or 5-hydroxymethyl furfural from the reaction vessel contents, and separating the insoluble humins.

* * * * *